US010557782B2

(12) United States Patent
Nowak et al.

(10) Patent No.: US 10,557,782 B2
(45) Date of Patent: Feb. 11, 2020

(54) PRESSURE CELL FOR RHEOLOGICAL EXPERIMENTS UNDER OSCILLATORY SHEAR AND PRESSURE

(71) Applicant: WATERS GMBH, Eschborn (DE)

(72) Inventors: Maik Nowak, Ludwigshafen (DE); Peter Schuler, Ludwigshafen (DE); Lorenz Siggel, Heidelberg (DE)

(73) Assignee: Waters GmbH, Eschborn (DE)

( * ) Notice: Subject to any disclaimer, the term of this patent is extended or adjusted under 35 U.S.C. 154(b) by 95 days.

(21) Appl. No.: 15/543,649

(22) PCT Filed: Jan. 13, 2016

(86) PCT No.: PCT/EP2016/050520
§ 371 (c)(1),
(2) Date: Jul. 14, 2017

(87) PCT Pub. No.: WO2016/113279
PCT Pub. Date: Jul. 21, 2016

(65) Prior Publication Data
US 2018/0266930 A1 Sep. 20, 2018

(30) Foreign Application Priority Data

Jan. 16, 2015 (EP) .................................. 15151531

(51) Int. Cl.
G01N 11/16 (2006.01)
(52) U.S. Cl.
CPC .............................. G01N 11/162 (2013.01)

(58) Field of Classification Search
CPC .... G01N 11/16; G01N 11/162; G01N 11/165; G01N 11/167
See application file for complete search history.

(56) References Cited

U.S. PATENT DOCUMENTS 4,484,468 A * 11/1984 Gau ........................ G01N 11/14
702/50
5,481,903 A * 1/1996 King .................... G01N 11/165
73/54.16

(Continued)

FOREIGN PATENT DOCUMENTS

| EP | 1 260 808 A1 | 11/2002 |
| WO | 97/42482 A1 | 11/1997 |

OTHER PUBLICATIONS

International Search Report dated Feb. 22, 2016 in PCT/EP2016/050520 filed Jan. 13, 2016.

(Continued)

*Primary Examiner* — Justin N Olamit
(74) *Attorney, Agent, or Firm* — Schmeiser, Olsen & Watts LLP

(57) ABSTRACT

Measuring device for measuring an elasticity and a viscosity of a medium, having a first measuring device part having a volume for receiving the medium to be measured, and a second measuring device part that protrudes into the volume, wherein the first measuring device part in relation to the second measuring device part is sealed by way of a gas flow seal, and wherein the first measuring device part in relation to the second measuring device part is movable in a rotating movement about a predefined axis.

12 Claims, 2 Drawing Sheets

(56) References Cited

U.S. PATENT DOCUMENTS

| | | | | |
|---|---|---|---|---|
| 5,874,665 | A * | 2/1999 | Larsson | G01N 11/14 |
| | | | | 73/54.28 |
| 6,167,752 | B1 | 1/2001 | Raffer | |
| 6,698,275 | B2 * | 3/2004 | Hall | G01N 11/14 |
| | | | | 73/54.28 |
| 9,574,983 | B2 * | 2/2017 | Santner | G01N 11/142 |
| 2004/0177679 | A1 | 9/2004 | Lahaut | |
| 2013/0226473 | A1 | 8/2013 | Murphy et al. | |
| 2015/0160111 | A1 * | 6/2015 | Lewis | G01N 11/162 |
| | | | | 73/54.41 |

OTHER PUBLICATIONS

International Preliminary Report on Patentability dated Jul. 27, 2017 in PCT/EP2016/050520 filed Jan. 13, 2016 (with English translation).

International Preliminary Report on Patentability and Written Opinion of the International Searching Authority dated Feb. 22, 2016 in PCT/EP2016/050520 filed Jan. 13, 2016 (with English translation of categories of cited documents).

* cited by examiner

PRESSURE CELL FOR RHEOLOGICAL EXPERIMENTS UNDER OSCILLATORY SHEAR AND PRESSURE

FIELD OF THE INVENTION

The present invention relates to a measuring device for measuring an elasticity and a viscosity of a medium, said measuring device permitting a measurement of the elasticity and of the viscosity of the medium even at high pressures or high temperatures, respectively. In particular, the invention relates to a device for measuring elasticities of low-viscosity liquids at high pressures and high temperatures.

BACKGROUND OF THE INVENTION

Viscosity measurements are known from the prior art, such as by way of measuring a pressure drop, a flow through a capillary, or by measuring a damping of an oscillation of a submerged probe. Furthermore, rotary rheometers for measuring viscosities are known. By way of measuring methods and measuring devices of this type it is indeed possible for the viscosity to be measured, occasionally even at high temperatures and high pressures; however, by way of measurements of this type it is impossible for elastic properties to be measured at a simultaneously low viscosity.

SUMMARY OF THE INVENTION

It can therefore be seen as an object of the invention to provide a device for measuring elasticities of a medium at high pressures or high temperatures, respectively, in particular a device for measuring elasticities of low-viscosity liquids at high pressures and high temperatures.

The object of the present invention is achieved by the subject matter of the independent claims, while advantageous refinements of the invention are embodied by the dependent claims.

According to one embodiment of the invention, a measuring device for measuring an elasticity and a viscosity of a medium is provided, wherein the measuring device has a volume for receiving the medium to be measured, said volume being delimited by a first measuring device part, a second measuring device part that protrudes into the volume, wherein the first measuring device part in relation to the second measuring device part is sealed by way of a gas flow seal, wherein the first measuring device part in relation to the second measuring device part is movable in a rotating movement about a predefined axis.

In this way, it is possible by virtue of the gas flow seal for the first measuring device part and the second measuring device part to be sealed in relation to one another in such a manner that the first measuring device part and the second measuring device part can be mutually rotated so as, based on this rotating movement, to determine an elasticity or a viscosity of a medium, respectively, said medium being located in a respective volume for receiving a medium to be measured. The gas flow seal enables mutual sealing of the two measuring device parts that is as low in friction as possible, or is substantially friction-free, respectively, to be provided such that the medium to be measured can be kept in the volume even under high pressures or at high temperatures, respectively, without the capability of movement of the first measuring device part and of the second measuring device part in relation to one another being significantly compromised. High temperatures in the context of the invention are understood to be temperatures up to approx. 200° C., and high pressures in the context of the invention are understood to be pressures up to approx. 16 bar (absolute).

The gas flow seal permits sealing of the volume such that the medium located therein can be measured even at high pressures and temperatures without however restricting or falsifying a measurement of torque by way of a solid gasket. A gas flow seal is distinguished by a three-way construction, wherein one way terminates in the volume to be sealed, and the two other ways serve for supplying gas or discharging gas, respectively. The sealing effect is achieved by way of a back pressure in the first way, said back pressure being generated by the throughflow of gas from the second to the third way. The first way is connected to the volume such that there is typically no gas flow in the volume. The specimen to be measured herein is located in the volume, wherein the volume is delimited by the first and the second measuring device part and is sealed by way of a gas flow seal. The volume that is delimited by the first and the second measuring device part is conceived for performing therein a viscosity measurement or an elasticity measurement. The gas flow herein serves for sealing, wherein the volume per se that receives the specimen to be measured in general is not exposed to a throughflow of air. Rather, the volume receives the liquid to be measured and holds the liquid. By contrast to an air bearing in which a constant flow through the barrier volume takes place, a static pressure is established in the interior of the measuring volume in the case of a gas flow seal. As opposed to an air bearing of rotating parts, in which a bearing requires tight gap dimensions, the gas flow seal seals a volume for receiving a specimen medium in relation to the external atmosphere. Furthermore, a gas flow seal on account of the dynamic flow principle enables the peripheral apparatuses such as drives and measuring devices to be kept outside a pressurized region, this not being readily possible in the case of a counter-pressure seal having a static pressure.

According to one embodiment of the invention, the volume in a region that is provided for receiving the medium to be measured is rotationally symmetrical, and the second measuring device part in that region that protrudes into that region of the volume that is provided for receiving the medium to be measured is rotationally symmetrical, wherein the first measuring device part has a hollow-cylindrical portion, and the second measuring device part has a cylindrical portion, wherein the hollow-cylindrical portion and the cylindrical portion in a region that is provided for receiving a medium to be measured form a cylindrical gap.

In this way, it is possible for a uniform rotating movement between the first measuring device part and the second measuring device part to be initiated, so as to enable a laminary and turbulence-free flow. It can be avoided on account of the rotational symmetry that by virtue of the rotating movement different pressure conditions arise within the volume in which the medium to be measured is located.

According to one embodiment of the invention, the rotating movement comprises an oscillating movement.

In this way, a supply line or a discharge line, respectively, for sensors or actuators can be provided on the first measuring device part or on the second measuring device part, respectively, without being subject to the issues of having to have the contacts of the respective devices follow the latter in the case of any rotation. In particular, the supply and discharge of media streams, such as liquid and gas lines, can be simplified when there is no revolving rotating movement but only an oscillatory rotating movement.

According to one embodiment of the invention, the oscillating movement has a sinusoidal oscillation.

In this way, a uniform oscillating movement which comprises a degree of acceleration of the first measuring device part in relation to the second measuring device part, or vice versa, that is as minor as possible can be provided between the first measuring device part and the second measuring device part. Furthermore, the measured values which in an oscillating movement are determined for measuring the elasticity and the viscosity can be evaluated in a simple manner when the oscillating behavior can be displayed in as simple a manner as possible, that is to say in the form of a sinusoidal oscillation, and the respective effects can thus be eliminated from the measured values.

According to one embodiment of the invention, the oscillating movement has a frequency between 0.01 Hz and 100 Hz.

In this way, dissimilar elasticity and viscosity properties of the medium to be measured can be taken into account, and the elasticity or viscosity, respectively, of the medium to be measured can be determined across the specified frequency range.

According to one embodiment of the invention, the oscillating movement has an amplitude between $1*10^{-6\circ}$ and $180°$.

In this way, maximum degrees of accuracy can be achieved in the measurement of the elasticity and of the viscosity of a medium to be measured. According to one embodiment of the invention, the oscillating movement has an amplitude between $5*10^{-5\circ}$ and $45°$, wherein $360°$ corresponds to the full circumference of a circle. According to one embodiment, the oscillation amplitude can be adapted to the medium to be measured in an iterative manner. To this end, the change in a measured torque on one measuring device part over the change in the oscillation amplitude of the other measuring device part can be used as the basis for actuating an actuator which initiates the oscillating movement in terms of the amplitude.

According to one embodiment of the invention, the measuring device has a torque sensor, wherein the torque sensor is provided on one of the first measuring device part and the second measuring device part.

In this way, the elasticity or the viscosity, respectively, of a medium to be measured can be determined by way of determining the torque that is required for setting the first measuring device part in rotary motion, in particular oscillatory motion, in relation to the second measuring device part.

According to one embodiment of the invention, one of the first measuring device part and the second measuring device part is fixed in relation to a reference point, and the torque sensor is provided on the fixed one of the first measuring device part and the second measuring device part.

In this way, the torque sensor can determine that torque in relation to the reference point that bears directly on the respective measuring device part without disturbing influences of an actuator influencing the measurement of the elasticity or of the viscosity, respectively. This applies in particular in the case in which the actuator is provided on the other measuring device part that is not fixed in relation to a reference point but, prompted by the actuator, moves in a rotating movement about the predefined axis in relation to that measuring device part that is fixed to the reference point.

According to one embodiment of the invention, the first measuring device part in the region of the gas flow seal has a first cylindrical sleeve portion and a second cylindrical sleeve portion, and the second measuring device part in the region of the gas flow seal has a first cylindrical portion and a second cylindrical portion, wherein the first cylindrical sleeve portion and the first cylindrical portion form a first cylindrical gap, and the second cylindrical sleeve portion and the second cylindrical portion form a second cylindrical gap, wherein a pressurized gas supply is provided between the first cylindrical gap and the second cylindrical gap.

In this way, it is possible for a pressurized gas to be supplied such that a build-up of pressure arises by way of the cylindrical gap that opens into the volume, and an outflow of the gases is performed by way of the other cylindrical gap in such a manner that on account of the flow resistance in the other cylindrical gap and in the respective gas supply a sustained pressure arises in the volume in which the medium to be measured is provided.

According to one embodiment of the invention, the pressurized gas supply is provided on the first measuring device part.

In this way, the gas supply can be provided on that part that is not connected to the torque sensor, such that no influence of the torque measurement on account of the coupling of the pressurized gas supply arises on the second measuring device part when the latter is fixed in relation to the reference point.

According to one embodiment of the invention, the first cylindrical sleeve portion and the second cylindrical sleeve portion of the first measuring device part and the pressurized gas supply conjointly form a unit which is capable of being separated from a cup of the first measuring device part that is provided for receiving the medium to be measured.

In this way, part of the first measuring device part indeed remains on the second measuring device part, but in this way the sealing geometry of the gas flow seal between the first and the second measuring device part, said sealing geometry being composed of the cylindrical gaps which is formed from the cylindrical portions of the second measuring device part and from the cylindrical sleeve portions of the first measuring device part, can be maintained. Moreover, the second measuring device part when the latter is fixed in relation to a reference point can remain in place while that part of the first measuring device part, for example in the form of a cup, that is removable from the pressurized gas supply can be removed. A medium in the cup, the latter representing substantially the volume for receiving the medium to be measured, can thus be replaced.

According to one embodiment of the invention, the second cylindrical gap on a side that faces away from the pressurized gas supply opens into the volume that is provided for receiving the medium to be measured.

In this way, the pressure in the volume can be sustained by supplying pressurized gas by way of the second cylindrical gap, such that media can be held and measured in the volume even at high temperatures or high pressures, respectively.

According to one embodiment of the invention, the measuring device has a temperature control device, wherein the volume for receiving the medium to be measured is capable of being temperature controlled by way of the temperature control device.

In this way, a temperature in the volume and thus a temperature of the medium to be measured can be set. This can be performed by way of a Peltier element, for example, such that to a certain degree both cooling as well as heating of the medium can be performed. For comparatively large temperature control ranges, an additional (or alternative) electric heating can be provided, for example. It is to be noted that further temperature control mechanisms can also be used for heating or cooling, for example by supplying a cooling liquid or a heating liquid, or a cooling gas or a heating gas, respectively.

According to one embodiment of the invention, the temperature control device has a Peltier element which is conceived and disposed in such a manner so as to control the temperature of the medium to be measured that is received in the volume.

Of course, the individual features described above can also be combined with one another, on account of which advantageous effects that exceed the sum of the individual effects can also be derived.

These and other aspects of the present invention will be explained and highlighted by reference to the exemplary embodiments described hereunder.

DETAILED DESCRIPTION OF EXEMPLARY EMBODIMENTS

Figure 1:
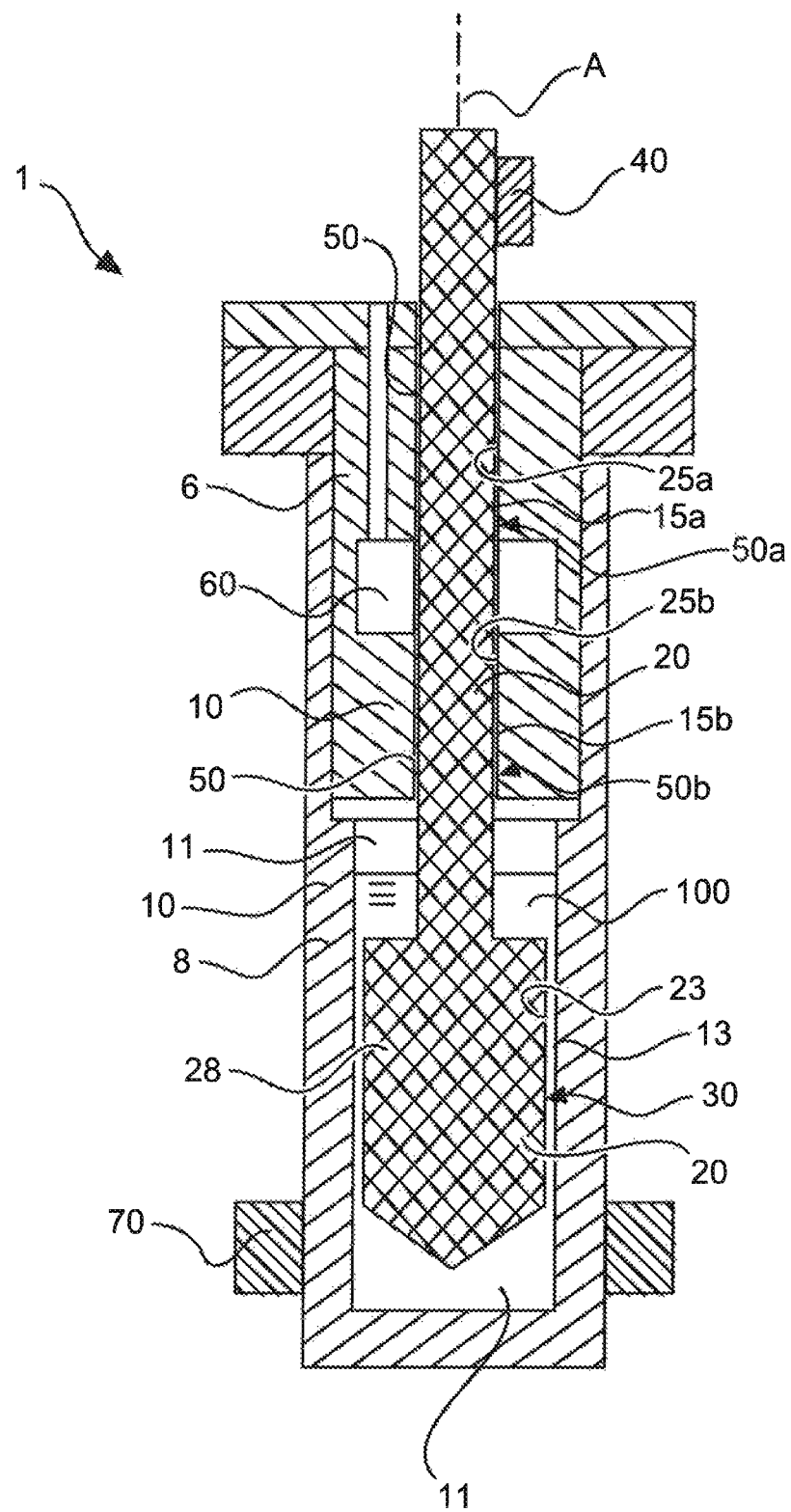
FIG. 1 shows a sectional view through an exemplary embodiment of a measuring device.

FIG. 1 shows a sectional view through a measuring device according to an exemplary embodiment of the invention. The measuring device shown in FIG. 1 has a first measuring device part 10 which in turn has a cup 8 in which the volume 11 in which the medium to be measured is received. The second measuring device part 20 herein plunges into the medium 100 to be measured, said second measuring device part 20 in that region in which the latter plunges into the medium 100 to be measured having a displacement body or cylinder 28, respectively. This displacement cylinder for avoiding secondary flows can converge to a point in the lower region, such as is specified in DIN 53019-1, for example. The first measuring device part 10 and the second measuring device part 20 are mutually rotatable along a rotation axis A. The second measuring device part 20 herein is fixed in relation to a reference point, for example, and the first measuring device part 10 is rotated in relation to the second measuring device part 20. A rheological property of the medium 100 to be measured can be determined via the prevailing torque by virtue of the mutual rotation of the two parts. Influence by the liquid properties of the medium 100 to be measured, the torque that in relation to the rotation axis A acts on the second measuring device part 20, acts between a cylindrical portion 23 of the second measuring device part 20 in the volume 11, on the one hand, and a hollow-cylindrical portion 13 of the first measuring device part 10 in the volume 11, on the other hand. In this way, the hollow-cylindrical portion 13 and the cylindrical portion 23 form a cylindrical sleeve portion, the walls of the latter being mutually rotated. The rheological properties of the medium, in particular the elasticity and the viscosity, can be derived from the resulting resistance and consequently from the prevailing torque. A torque sensor 40 can be provided herein on the second measuring device part 20, in particular when the second measuring device part is fixed in relation to a reference point. The most varied of types of torque sensors can be used herein, as long as said torque sensors are capable of determining a torque between the second measuring device 20 and the reference point and of providing adequate resolution. The cup 8 or the volume 11, respectively, can be temperature controlled by way of a temperature control device 70. This temperature control device 70 can be a Peltier element, for example, by way of which the cup 8 and thus the volume 11 can both be heated as well as cooled. In the case of only heating of the volume 11 having to be achieved, an electric heating device can also be provided as an alternative. It is to be noted that a combination of a Peltier element and an electric resistance heater can also be used, in particular when comparatively high temperatures are to be achieved. The temperature control device can be disposed in particular such that the former temperature controls the cup 8 on the wall regions that lie in the region of the medium to be filled, that is to say also along comparatively large wall portions as is shown in FIG. 1. In order to seal the first measuring device part 10 in relation to the second measuring device part 20 in a substantially friction-free or low-friction manner, respectively, a gas flow seal 50 is used between the first measuring device part and the second measuring device part. The gas flow seal is composed substantially by introducing a pressurized gas by way of a pressurized gas supply 6 via a pressurized gas supply 60 into cylindrical gaps 50a, 50b, the latter being formed by cylindrical sleeve portions 15a, 15b of the first measuring device part 10, on the one hand, and by cylindrical portions 25a, 25b of the second measuring device part 20, on the other hand. Proceeding from the pressurized gas supply 60, a second cylindrical gap 50b which extends from the pressurized gas supply 60 in the direction of the volume 11 is formed, wherein the second cylindrical gap 50b is formed by the cylindrical sleeve portion 15b of the first measuring device part 10 and by the second cylindrical portion 25b of the second measuring device part 20. Proceeding from the pressurized gas supply 60, a first cylindrical gap 50a extends in the opposite direction, wherein the first cylindrical gap 50a is formed by the first cylindrical sleeve portion 15a of the first measuring device part 10 and by the first cylindrical portion 25a of the second measuring device part 20. The gas flow seal 50 is now established by supplying a pressurized gas by way of the pressurized gas supply unit 6 to the pressurized gas supply 60, wherein the pressurized gas flows through the second cylindrical gap 50b in the direction of the volume 11 and builds up a pressure in the volume 11. Furthermore, the gas that is located in the pressurized gas supply 60 flows into the first cylindrical gap 50a, and by this way exits the measuring device 1 (upward in FIG. 1). On account of the flow resistance in the first cylindrical gap 50a and of the pressure of the pursuing gas in the pressurized gas supply, a pressure in the volume 11 is established by way of the gas pressure to be set in the pressurized gas supply, such that sealing of the volume 11 in relation to the external atmosphere is achieved in this way. Herein, a gas flow is performed only from the pressurized gas supply 60 into the second cylindrical gap 50a, while no substantial gas flow prevails in the cylindrical gap 50b. In this way, the second measuring device part 20, in particular the shaft of the second measuring device part 20 that leads out of the first measuring device part 10 and permits coupling to the reference point, can be guided with minor losses in relation to the first measuring device part 10. The sealing by way of the gas flow seal 50 herein has very little friction such that any influences on a measurement of torque at a torque sensor 40 by virtue of a drive (not shown here) of the first measuring device part 10 can be minimized. The drive (not shown) sets the first measuring device part 10 into rotary motion about the rotation axis A, while the second measuring device part 20 is fixed in relation to the reference point. As has already been stated above, measurements in the temperature range of up to approx. 200° C. and in the pressure range of up to approx. 16 bar (absolute) are possible with the measuring device shown in FIG. 1. A typical temperature range is approx. 150° C., and a typical pressure range is approx. 5 bar (absolute).

Figure 2:
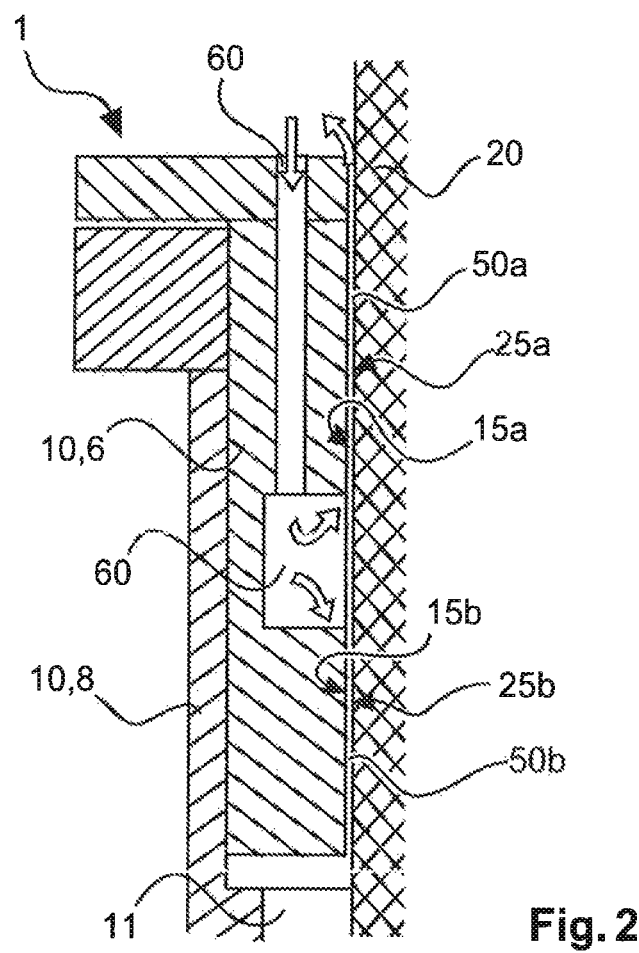
FIG. 2 shows a fragment of the sectional view of an exemplary embodiment of the measuring device, said sectional view showing a gas flow seal region.

FIG. 2 shows a fragment of the view as described above, said view showing in particular the part of the gas flow seal 50. It can again be seen from FIG. 2 that gas for the gas flow seal flows in through the pressurized gas supply unit 6 (double arrow) and then in the pressurized gas supply 60, for example in an annular chamber, that reaches around the respective shaft of the second measuring device part 20, flows into the cylindrical gaps 50a and 50b. The gas flow herein in the build-up of the pressure first is distributed into a part which flows in the second cylindrical gap 50b (downward in FIG. 2), and a part which flows in the first cylindrical gap 50a (upward in FIG. 2). As soon as the pressure has been built up in the volume 11, a substantially constant pressure is established in the volume 11 on account of the supply of the pressurized gas into the pressurized gas supply 60 and of that part of the gas that flows out through the first cylindrical gap 50a along the shaft of the second measuring device part 20. This pressure can be set by way of the pressure of the gas that is supplied by way of the pressurized gas supply unit 6. The first cylindrical gap 50a herein is formed by a first cylindrical portion 25a of the second measuring device part 20 and by a first cylindrical sleeve portion 15a of the first measuring device part 10. The second cylindrical gap 50b is formed by a second cylindrical portion 25b of the second measuring device part 20 and by a second cylindrical sleeve portion 15b of the first measuring device part 10. The first cylindrical sleeve portion 15a and the second cylindrical sleeve portion 15b herein can be provided on the pressurized gas supply unit 6, for example, the latter for the measurement in the volume 11 being fixedly connected to the cup 8 of the first measuring device part 10 but being able to be released from the cup 8 for changing the medium 100 to be measured in the volume 11. The pressurized gas supply unit 6 is indeed mounted so as to be rotatable in relation to the second measuring device part 20 but remains on the latter when the cup 8 is removed in order for the medium 100 to be measured in the cup 8 or in the volume 11 to be replaced, for example.

Figure 3:
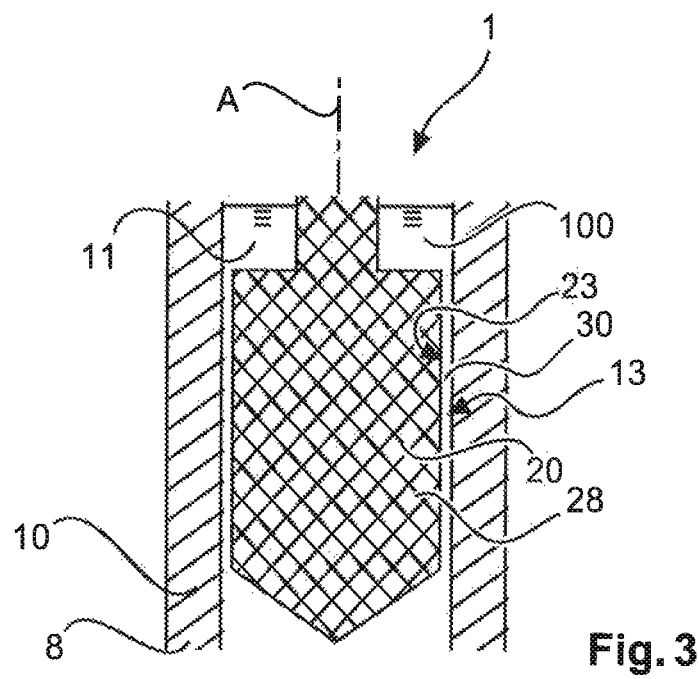
FIG. 3 shows a fragment of a sectional view of an exemplary embodiment of the measuring device, said sectional view showing the volume for receiving a medium to be measured.

FIG. 3 shows an enlarged sectional view in the region of the volume 11, the latter being delimited by the first measuring device part 10, in particular by the cup 8 of the first measuring device part 10, on the one hand, and by the displacement cylinder 28 of the second measuring device part 20. The displacement cylinder 28 has a cylindrical portion 23, while the cup 8 has a hollow-cylindrical portion 13. A cylindrical gap 30 in which the medium 100 to be measured is located is formed between the hollow-cylindrical portion 13 and the cylindrical portion 23. The movement or the resistance, respectively, between the rotating first measuring device part 10 and the stationary measuring device part 20 is defined substantially by the property of the liquid in the cylindrical gap 30. Depending on the liquid used therein, a torque which can be determined by the torque sensor 40 (cf. FIG. 1) is established in the case of an embossed rotating movement of the first measuring device part 10 on the second measuring device part 20. The displacement cylinder 28 can be removable from the part 20 by unscrewing, or can be connected to the latter in an integral manner.

It is to be noted that the term "comprise" does not exclude further elements or method steps, and the term "one" and "a" does not exclude a plurality of elements or steps.

The reference signs used serve only for enhancing the understandability and are not to be understood to be limiting in any way, wherein the scope of protection of the invention is reflected by the claims.

LIST OF REFERENCE SIGNS

1 Measuring device
6 Pressurized gas supply unit
8 Cup
10 First measuring device part
11 Volume for receiving a medium
13 Hollow-cylindrical portion of the first measuring device part in the volume
15a First cylindrical sleeve portion of the first measuring device part
15b Second cylindrical sleeve portion of the first measuring device part
20 Second measuring device part
23 Cylindrical portion of the second measuring device part in the volume
25a First cylindrical portion of the second measuring device part
25b Second cylindrical portion of the second measuring device part
28 Displacement cylinder
30 Cylindrical gap in the volume for receiving the medium to be measured
40 Torque sensor
50 Gas flow seal
50a First cylindrical gap
50b Second cylindrical gap
60 Pressurized gas supply
70 Temperature control device
100 Medium to be measured
A Axis, rotation axis

The invention claimed is:

1. A measuring device for measuring an elasticity and a viscosity of a medium, the measuring device comprising:
   a volume for receiving the medium to be measured, said volume being delimited by a first part,
   a second part that protrudes into the volume;
   wherein:
      the first part in relation to the second part is sealed by way of a gas flow seal, and
      the first part in relation to the second part is movable in a rotating movement and a predefined axis,
   wherein the gas flow seal comprises:
      the first part in a region of the gas flow seal has a first cylindrical sleeve portion and a second cylindrical sleeve portion,
      the second part in a region of the gas flow seal has a first cylindrical portion and a second cylindrical portion,
      the first cylindrical sleeve portion of the first part and the first cylindrical portion of the second part form a first cylindrical gap,
      the second cylindrical sleeve portion of the first part and the second cylindrical portion of the second part form a second cylindrical gap, and
      a pressurized gas supply is provided between the first cylindrical gap and the second cylindrical gap, wherein the second cylindrical gap on the side that faces away from the pressurized gas supply opens into the volume for receiving the medium to be measured and the measuring device is configured such that the pressurized gas flows out through the first cylindrical gap.

2. The measuring device is claimed in claim 1, wherein:
the volume is rotationally symmetrical,
the second part is rotationally symmetrical,
the first part has a hollow-cylindrical portion,
the second part has a cylindrical portion, and
the hollow-cylindrical portion and the cylindrical portion form a cylindrical gap.

3. The measuring device as claimed in claim 1, further comprising a drive to provide the rotating movement, which rotating movement comprises an oscillating movement.

4. The measuring device as claimed in claim 3, wherein the drive is configured such that the oscillating movement has a sinusoidal oscillation.

5. The measuring device as claimed in claim 4, wherein the drive is configured such that the oscillating movement has a frequency between 0.01 Hz and 100 Hz.

6. The measuring device as claimed in claim 4, wherein the drive is configured such that the oscillating movement has an amplitude between $5*10^{-5}°$ and $45°$.

7. The measuring device as claimed in claim 1, wherein:
the measuring device has a torque sensor, and
the torque sensor is provided on one of the first part and the second part.

8. The measuring device as claimed in claim 7, wherein:
one of the first part and the second part is fixed in relation to a reference point, and
the torque sensor is provided on the fixed one of the first part and the second part.

9. The measuring device is claimed in claim 1, wherein the pressurized gas supply is provided on the first part.

10. The measuring device as claimed in claim 9, wherein the first cylindrical sleeve portion and the second cylindrical sleeve portion of the first part and the pressurized gas supply conjointly form a unit which is capable of being separated from a cup of the first part that is provided for receiving the medium to be measured.

11. The measuring device as claimed in claim 1, wherein the measuring device has a first device, and the volume for receiving the medium to be measured is capable of being temperature controlled by way of the first device.

12. The measuring device is claimed in claim 11, wherein the temperature control device has a Peltier element which is conceived and disposed in such a manner so as to control the temperature of the volume for receiving the medium to be measured.

* * * * *